United States Patent
Bliss et al.

(10) Patent No.: US 9,421,601 B2
(45) Date of Patent: Aug. 23, 2016

(54) METHODS FOR FORMING AN ORTHOGONAL END ON A HELICAL STENT

(71) Applicant: Medtronic Vascular, Inc., Santa Rosa, CA (US)

(72) Inventors: Richard Bliss, Cloverdale, CA (US); Justin Goshgarian, Santa Rosa, CA (US); Rui Lam, Santa Rosa, CA (US); Padraig Savage, Galway (IE); Erik Griswold, Penngrove, CA (US); Giangranco Pellegrini, Santa Rosa, CA (US); Matthew Baldwin, Santa Rosa, CA (US); Lance Ensign, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 14/709,709

(22) Filed: May 12, 2015

(65) Prior Publication Data

US 2015/0239032 A1    Aug. 27, 2015

Related U.S. Application Data (62) Division of application No. 12/693,593, filed on Jan. 26, 2010, now Pat. No. 9,060,889.

(60) Provisional application No. 61/243,597, filed on Sep. 18, 2009, provisional application No. 61/243,578, filed on Sep. 18, 2009, provisional application No. 61/243,581, filed on Sep. 18, 2009, provisional application No. 61/243,582, filed on Sep. 18, 2009, provisional application No. 61/243,592, filed on Sep. 18, 2009, provisional application No. 61/243,600, filed on Sep. 18, 2009.

(51) Int. Cl.
| | |
|---|---|
| *B23K 31/02* | (2006.01) |
| *B21F 45/00* | (2006.01) |
| *A61F 2/88* | (2006.01) |
| *A61F 2/915* | (2013.01) |

(Continued)

(52) U.S. Cl.
CPC .............. *B21F 45/008* (2013.01); *A61F 2/88* (2013.01); *A61F 2/915* (2013.01); *B21F 1/04* (2013.01); *B21F 3/02* (2013.01); *B23K 31/027* (2013.01); *A61F 2002/91508* (2013.01); *A61F 2002/91525* (2013.01); *A61F 2002/91558* (2013.01); *B23K 2201/22* (2013.01); *Y10T 29/49826* (2015.01)

(58) Field of Classification Search
None
See application file for complete search history.

(56) References Cited

U.S. PATENT DOCUMENTS

| | | | |
|---|---|---|---|
| 2,153,936 | A | 4/1939 | Owens et al. |
| 3,185,185 | A | 5/1965 | Pfund |

(Continued)

FOREIGN PATENT DOCUMENTS

| | | | | |
|---|---|---|---|---|
| CA | 2408697 | A1 * | 11/2001 | ............... A61F 2/88 |
| EP | 0565251 | | 10/1993 | |

(Continued)

*Primary Examiner* — Kiley Stoner (57) ABSTRACT

A method of manufacturing a stent includes forming a wave form having a plurality of struts and a plurality of crowns. Each crown connects two adjacent struts. The wave form has a central portion and two end portions located on opposite sides the central portion. Some of the struts located in the end portions have lengths longer and/or shorter than an average length of all of the struts of the wave form. The method includes wrapping the wave form about a longitudinal axis to define a plurality of turns so that an end turn is oriented at an angle relative to the longitudinal axis, a second turn is at a first pitch angle that is less than the angle that the end turn is disposed relative to the longitudinal axis, a third turn is at a second pitch angle that is less than the first pitch angle, and a fourth turn is at a third pitch angle that is less than the second pitch angle.

13 Claims, 4 Drawing Sheets

(51) Int. Cl.
*B21F 1/04* (2006.01)
*B21F 3/02* (2006.01)

(56) References Cited

U.S. PATENT DOCUMENTS

| | | | |
|---|---|---|---|
| 4,047,544 A | 9/1977 | Seaborn et al. | |
| 4,886,062 A | 12/1989 | Wiktor | |
| 5,019,090 A | 5/1991 | Pinchuk | |
| 5,092,877 A | 3/1992 | Pinchuk | |
| 5,133,732 A | 7/1992 | Wiktor | |
| 5,226,913 A | 7/1993 | Pinchuk | |
| 5,304,200 A | 4/1994 | Spaulding | |
| 5,314,472 A | 5/1994 | Fontaine | |
| 5,324,472 A | 6/1994 | Page et al. | |
| 5,370,683 A | 12/1994 | Fontaine | |
| 5,443,498 A | 8/1995 | Fontaine | |
| 5,527,354 A | 6/1996 | Fontaine et al. | |
| 5,549,663 A * | 8/1996 | Cottone, Jr. | A61F 2/07 606/195 |
| 5,653,727 A | 8/1997 | Wiktor | |
| 5,716,396 A * | 2/1998 | Williams, Jr. | A61F 2/88 623/1.22 |
| 5,749,919 A * | 5/1998 | Blanc | A61F 2/88 606/194 |
| 5,876,432 A * | 3/1999 | Lau | A61F 2/88 606/191 |
| 5,891,507 A * | 4/1999 | Jayaraman | A61L 31/10 427/2.25 |
| 5,895,406 A | 4/1999 | Gray et al. | |
| 5,902,266 A | 5/1999 | Leone et al. | |
| 5,913,897 A * | 6/1999 | Corso, Jr. | A61F 2/91 623/1.15 |
| 5,925,061 A * | 7/1999 | Ogi | A61F 2/91 623/1.2 |
| 6,042,597 A * | 3/2000 | Kveen | A61F 2/91 623/1.15 |
| 6,117,165 A | 9/2000 | Becker | |
| 6,136,023 A | 10/2000 | Boyle | |
| 6,190,406 B1 | 2/2001 | Duerig et al. | |
| 6,203,569 B1 | 3/2001 | Wijay | |
| 6,342,067 B1 | 1/2002 | Mathis et al. | |
| 6,355,059 B1 | 3/2002 | Richter et al. | |
| 6,423,091 B1 | 7/2002 | Hojeibane | |
| 6,432,132 B1 | 8/2002 | Cottone et al. | |
| 6,447,540 B1 | 9/2002 | Fontaine et al. | |
| 6,503,270 B1 | 1/2003 | Richter et al. | |
| 6,610,086 B1 | 8/2003 | Kock et al. | |
| 6,656,219 B1 | 12/2003 | Wiktor | |
| 6,730,117 B1 | 5/2004 | Tseng et al. | |
| 6,736,844 B1 | 5/2004 | Glatt et al. | |
| 6,878,162 B2 | 4/2005 | Bales et al. | |
| 6,923,828 B1 | 8/2005 | Wiktor | |
| 6,969,402 B2 | 11/2005 | Bales et al. | |
| 7,004,968 B2 | 2/2006 | Lootz et al. | |
| 7,108,714 B1 | 9/2006 | Becker | |
| 7,169,175 B2 | 1/2007 | Cottone, Jr. et al. | |
| 7,329,277 B2 | 2/2008 | Addonizio et al. | |
| 7,988,717 B2 * | 8/2011 | Brown | A61F 2/91 606/108 |
| 2002/0022876 A1 * | 2/2002 | Richter | A61F 2/91 623/1.15 |
| 2002/0095208 A1 | 7/2002 | Gregorich et al. | |
| 2002/0103529 A1 * | 8/2002 | Pinchasik | A61F 2/91 623/1.15 |
| 2002/0156523 A1 * | 10/2002 | Lau | A61F 2/88 623/1.13 |
| 2003/0065383 A1 * | 4/2003 | Pinchasik | A61F 2/91 623/1.15 |
| 2003/0083736 A1 | 5/2003 | Brown et al. | |
| 2004/0044401 A1 | 3/2004 | Bales et al. | |
| 2004/0143318 A1 | 7/2004 | Tseng et al. | |
| 2004/0167608 A1 * | 8/2004 | Cheng | A61F 2/91 623/1.15 |
| 2004/0176837 A1 * | 9/2004 | Atladottir | A61F 2/856 623/1.35 |
| 2005/0149168 A1 * | 7/2005 | Gregorich | A61F 2/91 623/1.15 |
| 2006/0030934 A1 | 2/2006 | Hogendijk et al. | |
| 2006/0079955 A1 | 4/2006 | Brown | |
| 2007/0005126 A1 * | 1/2007 | Tischler | A61F 2/91 623/1.15 |
| 2007/0219618 A1 * | 9/2007 | Cully | A61F 2/88 623/1.13 |
| 2008/0097580 A1 | 4/2008 | Dave | |
| 2008/0097582 A1 | 4/2008 | Shanley et al. | |
| 2008/0183273 A1 | 7/2008 | Mesana et al. | |
| 2008/0206440 A1 * | 8/2008 | Cottone | A61F 2/915 427/2.24 |
| 2008/0215133 A1 * | 9/2008 | Richter | A61F 2/856 623/1.16 |
| 2008/0288053 A1 | 11/2008 | Addonizio et al. | |
| 2008/0289389 A1 | 11/2008 | Fitch et al. | |
| 2008/0294241 A1 | 11/2008 | Addonizio et al. | |
| 2008/0306583 A1 | 12/2008 | Bashiri et al. | |
| 2008/0319529 A1 | 12/2008 | Krivoruchko et al. | |
| 2008/0319534 A1 * | 12/2008 | Birdsall | A61F 2/88 623/1.22 |
| 2008/0319535 A1 | 12/2008 | Craven et al. | |
| 2009/0005848 A1 | 1/2009 | Strauss et al. | |
| 2009/0024207 A1 | 1/2009 | Addonizio et al. | |
| 2009/0036976 A1 | 2/2009 | Beach et al. | |
| 2009/0054972 A1 * | 2/2009 | Norton | A61F 2/90 623/1.53 |
| 2010/0070022 A1 * | 3/2010 | Kuehling | A61F 2/82 623/1.16 |
| 2010/0234936 A1 * | 9/2010 | Schlun | A61F 2/88 623/1.22 |
| 2010/0274350 A1 * | 10/2010 | Richter | A61F 2/91 623/1.16 |
| 2011/0022156 A1 * | 1/2011 | Richter | A61F 2/91 623/1.16 |
| 2011/0093059 A1 * | 4/2011 | Fischell | A61F 2/91 623/1.15 |
| 2011/0218615 A1 * | 9/2011 | Griswold | A61F 2/88 623/1.15 |
| 2011/0251668 A1 * | 10/2011 | Thompson | A61F 2/90 623/1.15 |
| 2011/0264195 A1 * | 10/2011 | Griswold | A61F 2/915 623/1.22 |
| 2012/0018496 A1 * | 1/2012 | Carmody | B21F 1/04 228/173.5 |
| 2012/0041540 A1 * | 2/2012 | Shobayashi | A61F 2/91 623/1.15 |
| 2012/0067008 A1 * | 3/2012 | Bienvenu | A61L 31/121 53/452 |
| 2012/0071962 A1 * | 3/2012 | Huang | A61F 2/91 623/1.16 |
| 2013/0282107 A1 * | 10/2013 | Baldwin | A61F 2/88 623/1.22 |
| 2015/0039072 A1 * | 2/2015 | Beach | A61F 2/915 623/1.2 |
| 2015/0039075 A1 * | 2/2015 | Abunassar | A61F 2/915 623/1.15 |
| 2015/0209167 A1 * | 7/2015 | Mangiardi | B23K 26/38 623/1.17 |

FOREIGN PATENT DOCUMENTS

| | | |
|---|---|---|
| EP | 945107 | 9/1999 |
| EP | 1155664 | 11/2007 |
| GB | 2281865 | 3/1995 |
| WO | WO2007/095466 | 8/2007 |
| WO | WO2008/028964 | 3/2008 |
| WO | WO2008/049045 | 4/2008 |
| WO | WO2008/100783 | 8/2008 |

* cited by examiner

METHODS FOR FORMING AN ORTHOGONAL END ON A HELICAL STENT

CROSS-REFERENCE TO RELATED APPLICATIONS

This application is a Division of and claims the benefit of priority from U.S. patent application Ser. No. 12/693,593, filed Jan. 26, 2010, now allowed, which claims the benefit of priority from U.S. Provisional Patent Application Ser. No. 61/243,597, filed on Sep. 18, 2009, the entire content of which is incorporated herein by reference. This application also claims the benefit of priority from U.S. Provisional Patent Application Ser. Nos. 61/243,578, 61/243,581, 61/243,582, 61/243,592, and 61/243,600, all filed on Sep. 18, 2009, the entire contents of all of which are incorporated herein by reference.

BACKGROUND OF THE INVENTION

1. Field of the Invention

The present invention is generally related to a method of manufacturing a helical stent having an orthogonal end relative to a longitudinal axis of the stent, as well as to a helical stent having an end that is orthogonal to the longitudinal axis of the stent.

2. Background of the Invention

A stent is typically a hollow, generally cylindrical device that is deployed in a body lumen from a radially contracted configuration into a radially expanded configuration, which allows it to contact and support a vessel wall. A plastically deformable stent can be implanted during an angioplasty procedure by using a delivery system that includes a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter.

Stents may be formed from wire(s), may be cut from a tube, or may be cut from a sheet of material and then rolled into a tube-like structure. While some stents may include a plurality of connected rings that are substantially parallel to each other and are oriented substantially perpendicular to a longitudinal axis of the stent, others may include a helical coil that is wrapped around the longitudinal axis at a non-perpendicular angle. Helical stents tend to have ends that are not perpendicular to the longitudinal axis due to the pitch of the helix. To square off the ends of a helical stent, the last turn at either end may include a wave form that includes waves of varying amplitudes. However, by varying the amplitudes of the waves, the stent may exhibit non-uniform behavior as the stent is crimped onto a balloon and/or expanded at the deployment site.

SUMMARY OF THE INVENTION

It is desirable to provide a helical stent that is configured to contract and expand more uniformly, so that a "dog bone" effect during expansion may be substantially eliminated.

It is an aspect of the present invention to provide a method of manufacturing a stent. The method includes forming a wave form having a plurality of struts and a plurality of crowns. Each crown connects two adjacent struts. The wave form has a central portion and two end portions located on opposite sides of the central portion. In an embodiment, some of the struts located in the end portions may have lengths longer than an average length of all of the struts of the wave form. In an embodiment, some of the struts located in the end portions may have lengths shorter than an average length of all of the struts of the wave form. The method includes wrapping the wave form about a longitudinal axis to define a plurality of turns so that a first turn is oriented at an angle relative to the longitudinal axis, a second turn is at a first pitch angle that is less than the angle that the first turn is disposed relative to the longitudinal axis, a third turn is at a second pitch angle that is less than the first pitch angle, and a fourth turn is at a third pitch angle that is less than the second pitch angle. In an embodiment, the first turn is substantially perpendicular to the longitudinal axis, i.e., the angle that the first turn is disposed relative to the longitudinal axis is about 90°. In an embodiment, the first turn is not substantially perpendicular to the longitudinal axis and instead has a pitch angle that is greater than 90°, and the second turn is at a pitch angle that is less than the pitch angle of the first turn, and so on.

It is an aspect of the present invention to provide a stent that includes a wave form comprising a plurality of struts and a plurality of crowns. Each crown connects two adjacent struts within the wave form. The wave form is wrapped around a longitudinal axis to define a central portion and two end portions located on opposite sides of the central portion. The central portion comprises a plurality of turns oriented at a first pitch angle relative to the longitudinal axis. The end portions each comprise a plurality of turns oriented at different pitch angles, and an end turn oriented substantially perpendicular to the longitudinal axis. The different pitch angles of the end portions are between the first pitch angle and about 90°. In an embodiment, the end turn is not oriented substantially perpendicular to the longitudinal axis and instead has a pitch angle that is greater than 90°, and the turns in the end portions have pitch angles that gradually transition from the pitch angle of the end turn to the first pitch angle.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EMBODIMENTS OF THE INVENTION

The following detailed description is merely exemplary in nature and is not intended to limit the invention or the application and use of the invention. Furthermore, there is no intention to be bound by any expressed or implied theory presented in the preceding technical field, background, brief summary or the following detailed description.

Figure 1:
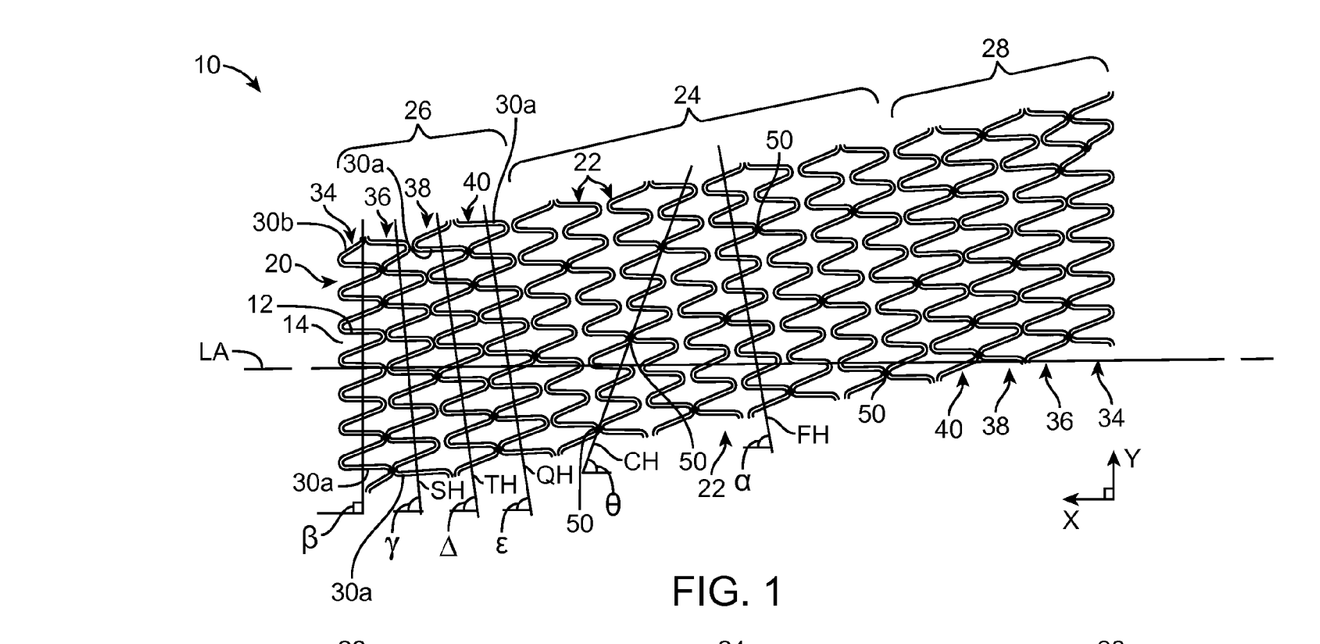
FIG. 1 schematically depicts a stent according to an embodiment of the present invention in an unrolled configuration.
Figure 2:
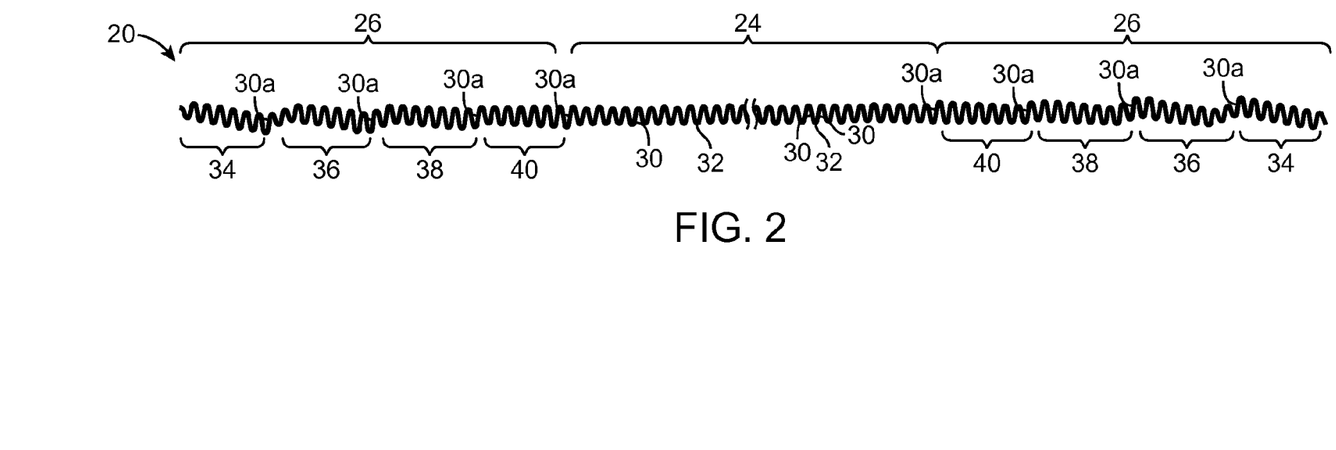
FIG. 2 schematically depicts a wave form for the stent of FIG. 1 before the wave form is wrapped around a longitudinal axis to define the stent of FIG. 1.

FIG. 1 illustrates a stent 10 according to an embodiment of the present invention. Although the stent 10 is generally cylindrical in shape and has a longitudinal axis LA extending through the center of the stent 10, FIG. 1 illustrates the stent 10 in an "unrolled" state, which may be created when the stent 10 is slit from one end to the other along an axis that is parallel to the longitudinal axis LA. The stent 10 includes a continuous wave form 20, an embodiment of which is illustrated in FIG. 2, that includes a plurality of turns 22 that are created when the wave form 20 is wrapped around the longitudinal axis LA during manufacturing of the stent 10. A mandrel or rod that is aligned with the longitudinal axis LA may be used to support the wave form 20 as the wave form 20 is wrapped around the longitudinal axis LA. The stent 10 generally includes a central portion 24 and two end portions, a first end portion 26 and a second end portion 28, that are located on opposite sides of the central portion 24. In an embodiment, the first end portion 26 and the second end portion 28 may be mirror images of each other.

As illustrated in FIG. 2, the wave form 20 includes a plurality of struts 30 and a plurality of crowns 32. Each crown 32 is a curved portion or turn within the wave form 20 that connects adjacent struts 30 to define the continuous wave form 20. As shown in FIG. 2, the struts 30 are substantially straight portions of the wave form 20. In other embodiments, the struts 30 may be slightly bent or have other shapes, such as a sinusoidal wave, for example.

As illustrated in FIG. 1, the wave form 20 is wrapped around the longitudinal axis LA at different pitches so that the wave form 20 generally defines a helical coil in the central portion 24 having a first helical angle, or first pitch angle $\alpha$, to define a first helix FH, and also defines ends that are substantially square or perpendicular with the longitudinal axis LA. As illustrated, the first end portion 26, include a first turn 34 that is wrapped about the longitudinal axis LA at an angle $\beta$ of about 90° so that the stent 10 has an end that is substantially orthogonal or perpendicular to the longitudinal axis LA. In an embodiment, the angle $\beta$ is greater than 90°.

The number of turns 22 about the longitudinal axis and the first helical angle $\alpha$ may be determined by the particular specifications of the stent 10, such as the desired unexpanded and expanded diameters and the length of the stent, as well as the size (e.g., diameter) and particular material of the wire or strip of material that may be used to create the wave form 20. The illustrated embodiments are not intended to be limiting in any way.

The first end portion 26 also includes a second turn 36 that is a continuation of the wave form 20 from the first turn 34. The second turn 36 is wrapped about the longitudinal axis LA at a second pitch angle $\gamma$ that is less than 90° but greater than the first pitch angle $\alpha$, to define a second helix SH. Additional turns may be part of the first end portion 26, such as a third turn 38, and a fourth turn 40, and may be configured to provide a more gradual transition between the first turn 34 that is wrapped about the longitudinal axis LA at about 90° and the first pitch $\alpha$ of the central portion 24. In the illustrated embodiment, the third turn 38 is wrapped about the longitudinal axis LA at a third pitch angle $\Delta$, which is greater than the first pitch angle $\alpha$ but less than the second pitch angle $\gamma$, to define a third helix TH, and the fourth turn 40 is wrapped about the longitudinal axis LA at a fourth pitch angle $\epsilon$, which is greater than the first pitch angle $\alpha$ but less than the third pitch angle $\gamma$, to define a fourth helix QH. Although three transitional turns 36, 38, 40 are illustrated in the embodiment of FIG. 1, more or less transitional turns may be used. The illustrated embodiment is not intended to be limiting in any way.

As illustrated, each of the turns 34, 36, 38, 40 of the first end portion 26 include struts 30 having different lengths, and some of the struts 30 have a length that is longer, labeled 30a in FIG. 1, than the average length of all of the struts 30 of the stent 10. It is desirable to have the length of the longest strut 30a of any given turn 34, 36, 38, 40 to be as short as possible, yet provide the desired transition in pitch angle. The presence of the longer struts 30a in the first end portion 26 allow for the transition from the orthogonal end to the helical central portion 24, but may cause the stent 10 to expand unevenly, as compared to central portion 24, when an internal pressure is applied to the stent 10. It may be desirable to connect the crown 32 that connects a longer strut 30a within a turn 22 to a crown 32 of the next turn in order to impede the expansion of the part of the wave form 20 that contains the longer strut 30a. In an embodiment, some of the struts located in the first end portion 26 may have lengths that are shorter, labeled 30b in FIG. 1, than an average length of all of the struts 30 of the stent 10.

The stent 10 also includes a plurality of connections 50 that are configured to connect selected crowns 32 of adjacent turns 22 so that when the stent is in an unexpanded condition, the plurality of connections 50 generally lie along a connection helix CH defined by a connection helical angle $\theta$ relative to the longitudinal axis LA. As illustrated in FIG. 1, the connection helix CH is oriented substantially opposite to the first helix FH described above such that the connection helical angle $\theta$ is between 0° and 90° when using a coordinate system that is opposite the coordinate system depicted in FIG. 1 (i.e., the positive x axis runs from left to right rather than from right to left).

The connections 50 may be created by fusing the selected crowns 32 together. As used herein, "fusing" is defined as heating the target portions of materials to be fused together, without adding any additional material, to a level where the material in the target portions flow together, intermix with one another, and form a fusion when the materials cool down to, for example, room temperature. A suitable laser may be used to create the fusion.

In an embodiment, the connections 50 may be created by welding or soldering the selected crowns 32 together. As used herein, "welding" and "soldering" are defined as heating an additional material that is separate from the selected crowns and applying the heated additional material to the selected crowns 32 so that when the additional material cools, the selected crowns 32 are welded or soldered together.

In an embodiment, the connections 50 may be created by fusing, welding, or soldering an additional piece of material (not shown) that extends between selected crowns 32. The additional piece of material may resemble a strut or a portion of a strut, and may be sized to provide spacing between the selected crowns of two adjacent turns, if desired. The illustrated embodiments are not intended to be limiting in any way.

The size of the connections 50 may also be varied according to the desired flexibility and rate of expansion for a given area of the stent 10. In general, the larger the connection 50, i.e. the larger the fusion or weld, the greater the stiffness, and the slower the rate of expansion of the stent in the area of the larger connections.

Figure 3:
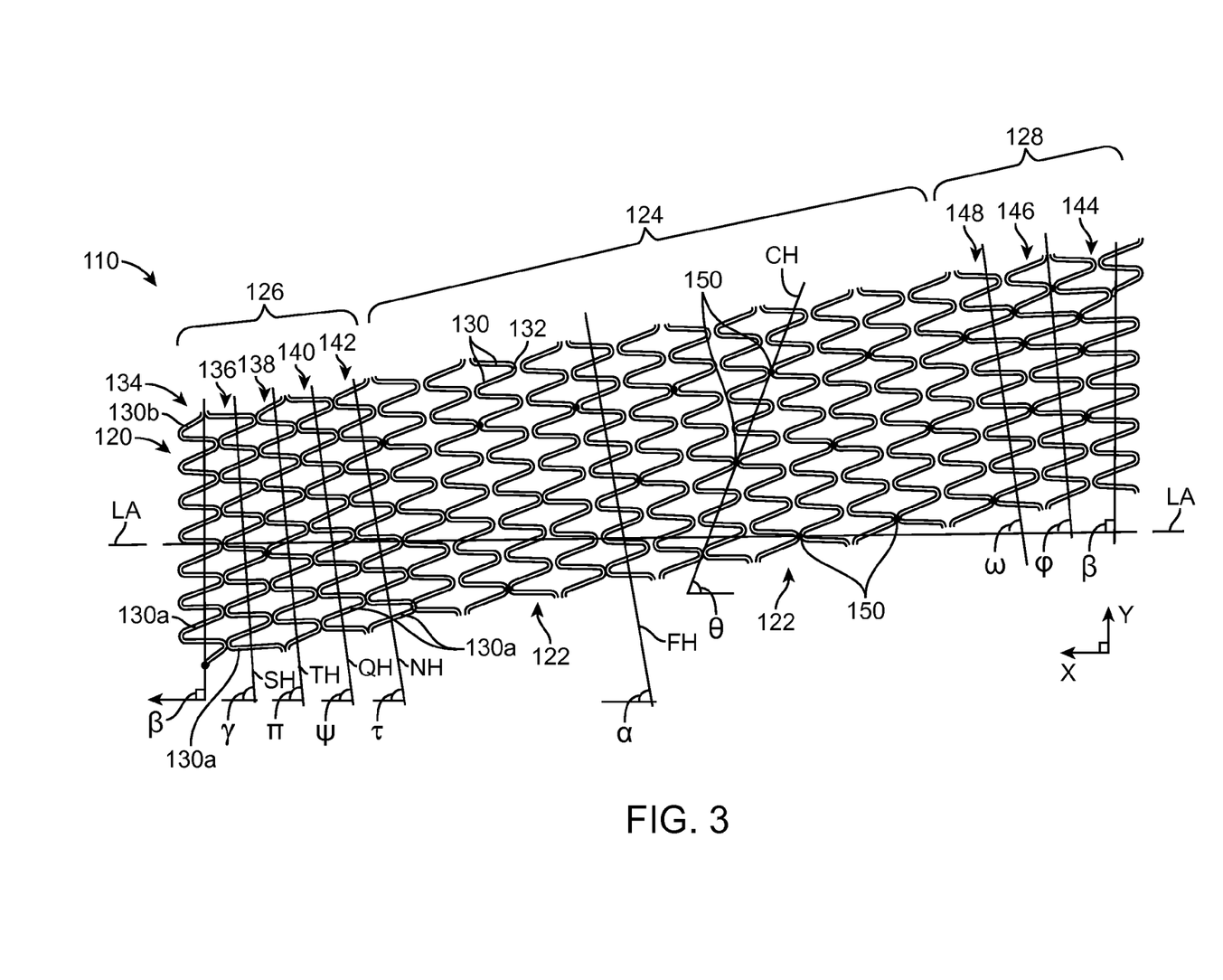
FIG. 3 schematically depicts a stent according to an embodiment of the present invention in an unrolled configuration.

FIG. 3 illustrates a stent 110 according to an embodiment of the present invention an "unrolled" state. The stent 110 includes a continuous wave form 120 that includes a plurality of turns 122 that are created when the wave form 120 is wrapped around the longitudinal axis LA during manufacturing of the stent 110. The stent 110 generally includes a central portion 124 and two end portions, a first end portion 126 and a second end portion 128, that are located on opposite sides of the central portion 124.

As illustrated in FIG. 3, the wave form 120 includes a plurality of struts 130 and a plurality of crowns 132. Each crown 132 is a curved portion or turn within the wave form 120 that connects adjacent struts 130 to define the continuous wave form 120. As shown in FIG. 3, the struts 130 are substantially straight portions of the wave form 120. In other embodiments, the struts 130 may be slightly bent or have other shapes, such as a sinusoidal wave, for example.

As illustrated in FIG. 3, the wave form 120 is wrapped around the longitudinal axis LA at different pitches so that the wave form 120 generally defines a helical coil in the central portion 124 having a first helical angle, or first pitch angle α, to define a first helix FH, and also defines ends that are substantially square or perpendicular with the longitudinal axis LA. As illustrated, the first end portion 126, include a first turn 134 that is wrapped about the longitudinal axis LA at an angle β of about 90° so that the stent 110 has an end that is substantially square or perpendicular to the longitudinal axis LA. In an embodiment, the angle β may be greater than 90°.

The number of turns 122 about the longitudinal axis and the first helical angle α may be determined by the particular specifications of the stent 110, such as the desired unexpanded and expanded diameters and the length of the stent, as well as the size (e.g., diameter) and particular material of the wire or strip of material. The illustrated embodiments are not intended to be limiting in any way.

The first end portion 126 also includes a second turn 136 that is a continuation of the wave form 120 from the first turn 134. The second turn 136 is wrapped about the longitudinal axis LA at a second pitch angle ρ that is less than 90° but greater than the first pitch angle α, to define a second helix SH. Additional turns may be part of the first end portion 126, such as a third turn 138, and a fourth turn 140, and a fifth turn 142, and may be configured to provide a more gradual transition between the first turn 134 that is wrapped about the longitudinal axis LA at about 90° and the first pitch angle α of the central portion 124. In the illustrated embodiment, the third turn 138 is wrapped about the longitudinal axis LA at a third pitch angle π, which is greater than the first pitch angle α but less than the second pitch angle ρ, to define a third helix TH. The fourth turn 140 is wrapped about the longitudinal axis LA at a fourth pitch angle Ψ, which is greater than the first pitch angle α but less than the third pitch angle π, to define a fourth helix QH. The fifth turn 142 is wrapped about the longitudinal axis LA at a fifth pitch angle τ, which is greater than the first pitch angle α but less than the fourth pitch angle π, to define a fifth helix NH.

As illustrated, each of the turns 134, 136, 138, 140, 142 of the first end portion 126 include struts 130 having different lengths, and some of the struts 130 have a length that is longer, labeled 130a in FIG. 3, than the average length of all of the struts 130 of the stent 110. It is desirable to have the length of the longest strut 130a of any given turn 134, 136, 138, 140, 142 to be as short as possible, yet provide the desired transition in pitch angle.

The presence of the longer struts 130a in the first end portion 126 allow for the transition from the orthogonal end to the helical central portion 124, but may cause the stent 110 to expand unevenly, as compared to central portion 124, when an internal pressure is applied to the stent 110. It may be desirable to connect the crown 132 that connects a longer strut 130a within a turn 122 to a crown 132 of the next turn in order to stiffen that area and impede the expansion of the part of the wave form 120 that contains the longer strut 130a. In an embodiment, some of the struts located in the first end portion 126 may have lengths that are shorter, labeled 130b in FIG. 3, than an average length of all of the struts 130 of the stent 110. By using additional transition turns in the end portion 126 of the stent 110 illustrated in FIG. 3, as compared to the end portion 26 of the stent 10 illustrated in FIG. 1, the longer struts 130a illustrated in FIG. 3 may be shorter than the longer struts 30a illustrated in FIG. 1.

The stent 110 also includes a plurality of connections 150 that are configured to connect selected crowns 312 of adjacent turns 122 so that when the stent is in an unexpanded condition, the plurality of connections 150 generally lie along a connection helix CH defined by a connection helical angle θ relative to the longitudinal axis LA. As illustrated in FIG. 3, the connection helix CH is oriented substantially opposite to the first helix FH described above such that the connection helical angle θ is between 0° and 90° when using a coordinate system that is opposite the coordinate system depicted in FIG. 3 (i.e., the positive x axis runs from left to right rather than from right to left).

As also illustrated in FIG. 3, the end portions 126, 128 are not necessarily mirror images of each other. The end portion 126 includes a total of five turns 134, 136, 138, 140, 142, while the end portion 128 only includes three turns 144, 146, 148. The end turn 144 of the end portion 128 has a pitch angle β of about 90° so that the end of the end portion 128 is substantially perpendicular to the longitudinal axis LA. In an embodiment, the end turn of the end portion 128 has a pitch angle that is greater than 90°. The next turn 146 is wrapped about the longitudinal axis LA at a pitch angle φ, which is less than the angle β (i.e., ~90°), but greater than the first pitch angle α of the central portion 124. The next turn 148 is wrapped about the longitudinal axis LA at a pitch angle ω, which is less than the pitch angle φ of the turn 146, but greater than the first pitch angle α of the central portion 124.

Of course, any number of transition turns may be in each end portion 126, 128 to transition the helix of the central portion 124 to an orthogonal end. In an embodiment, the central portion of stent consists of a series of transitions so that the entire stent is made up of transitions and each turn includes struts of different lengths, and no two adjacent turns have the same pitch angle. The illustrated embodiments are not intended to be limiting in any way.

The change in pitch angle from turn to turn within a transition, such as within the end portions 26, 28, 126, 128 discussed above and illustrated in FIGS. 1 and 3, is constant and can be calculated as the difference between the pitch angle of the end turn and the pitch angle of the central portion divided by the number of transition turns in between the end turn and the central portion, or:

$$\text{change in pitch angle} = (\beta - \alpha)/\# \text{ transition turns} \quad (1)$$

Using equation 1, the various pitch angles for the turns 36, 38, 40 of FIG. 1 and for the turns 136, 138, 140, 142, 146, 148 of FIG. 3 may be calculated. In an embodiment, the change in pitch angle between adjacent turns may not be constant.

Figure 4:
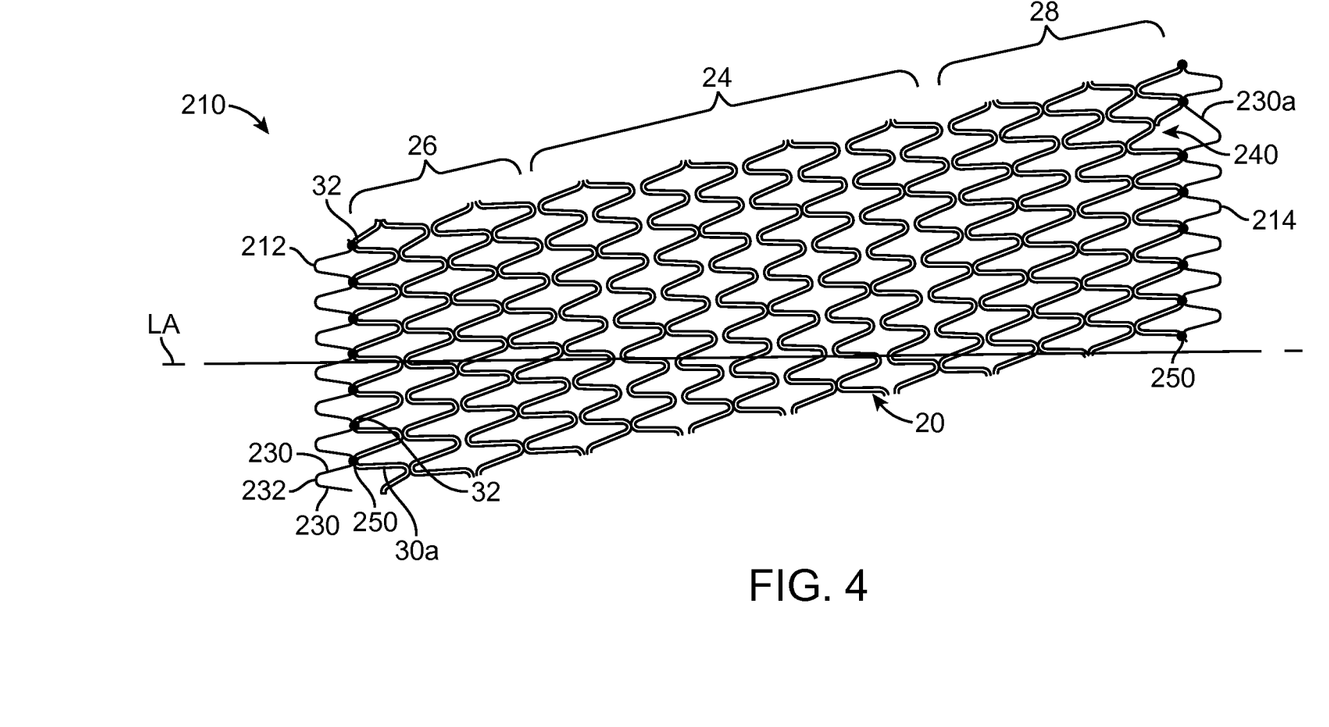
FIG. 4 schematically depicts a stent according to an embodiment of the present invention in an unrolled configuration.

FIG. 4 illustrates and embodiment of a stent 210 that is substantially similar to the stent 10 of FIG. 1, but with additional end segments 212, 214 that are connected to each end portion 26, 28 of the wave form 20. The end segments 212, 214 may be formed separate from the wave form 20 and may be connected to the end portions 26, 28 of the wave form 20 after the wave form 20 has been wrapped around the longitudinal axis LA. The end segments 212, 214 may be formed from a wire or other suitable strip of material, or may be cut from a tube or sheet of material and rolled into a ring-like structure.

As illustrated in FIG. 4, the end segment 212 includes a plurality of struts 230 having substantially the same length and a plurality of crowns 232 having substantially same size. Each crown 232 connects adjacent struts 230 so as to form a continuous ring having a constant length along the longitudinal axis LA. The end segment 212 may be connected to the wave form 20 portion of the stent 210 with a plurality of connections 250. In the illustrated embodiment, every crown 32 of the end portion 26 of the wave form 20 is connected to a corresponding crown 232 of the end segment 212. The end segment 212 may assist in controlling expansion of the areas of the end portion 26 that include the longer struts 30$a$ so that the end of the stent 210 expands more uniformly with the rest of the stent 210.

The end segment 214 may have substantially the same design as the end segment 212, or the end segment 214 may have a different design to compensate for the end of the wave form 20, as illustrated in FIG. 4. For example, the end segment 214 may include a longer strut 230$a$ to bridge a gap 240 that is created due to the end of the wave form 20. Other configurations of the end segment 212, 214 in accordance with embodiments of the present invention are contemplated, and the illustrated embodiment is not intended to be limiting in any way.

Figure 5:
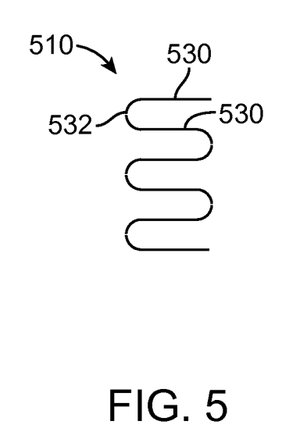
FIG. 5 schematically depicts an end turn of a stent according to an embodiment of the present invention in an unexpanded condition.

In addition to having the ends of the stent orthogonal to the longitudinal axis LA of the stent, as well as having substantially uniform expansion properties upon deployment, it is also desirable for the ends of the stent to be well opposed to the vessel wall when the stent is deployed at the target deployment site. It has been found that the greater the angle of strut deployment, the greater the propensity of the deployed struts to protrude outwardly. FIG. 5 illustrates an end turn 510 of a stent in accordance with an embodiment of the invention. The end turn 510 includes a plurality of struts 530 and a plurality of crowns 532 that connect adjacent struts 530 of the end turn 510 to each other. In an embodiment, the end segment 212 of the stent 210 of FIG. 4 includes the end turn 510 of FIG. 5.

Figure 6:
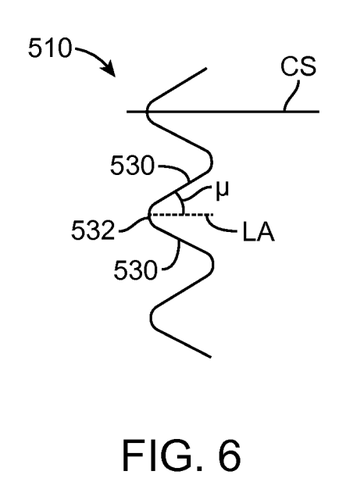
FIG. 6 schematically depicts the end turn of the stent of FIG. 5 in an expanded condition.

The struts 530 and the crowns 532 are configured to provide a deployment angle $\mu$, illustrated in FIG. 6, of at least 40°. The deployment angle $\mu$ is defined as the angle between the longitudinal axis LA of the stent and one of the struts 530 when the crowns 132 and struts 130 have started to plastically deform so that when the internal pressure is relieved from the stent, the crowns 532 and struts 530 remain in the same position and do not contract towards the longitudinal axis LA. It has been found that designing the crowns 532 and struts 530 to have a deployment angle of at least 40° allows the struts 530 to protrude outwardly from the outer circumferential surface of the rest of the stent (schematically depicted in FIG. 6 as line CS), which may allow the end of the stent to be well opposed to the vessel wall when the stent is deployed at the target deployment site.

The embodiments of the stents discussed above may be formed from a wire or a strip of suitable material. In certain embodiments, the stents may be formed, i.e., etched or cut, from a thin tube of suitable material, or from a thin plate of suitable material and rolled into a tube. Suitable materials for the stent include but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the stent may be formed from a cobalt alloy, such as L605 or MP35N®, Nitinol (nickel-titanium shape memory alloy), ABI (palladium-silver alloy), Elgiloy® (cobalt-chromium-nickel alloy), etc. It is also contemplated that the stent may be formed from two or more materials that are laminated together, such as tantalum that is laminated with MP35N®. The stents may also be formed from wires having concentric layers of different materials. Embodiments of the stent may also be formed from hollow tubes, or tubes that have been filled with other materials. The aforementioned materials and laminations are intended to be examples and are not intended to be limiting in any way.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient roadmap for implementing an exemplary embodiment of the invention, it being understood that various changes may be made in the function and arrangement of members described in an exemplary embodiment without departing from the scope of the invention as set forth in the appended claims.

What is claimed is:

1. A method of manufacturing a stent, the method comprising:

forming a wave form having a plurality of struts and a plurality of crowns, each crown connecting two adjacent struts, the wave form having a central portion and two end portions located on opposite sides the central portion, some of the struts located in the end portions have lengths longer and/or shorter than an average length of all of the struts of the wave form; and wrapping the wave form about a longitudinal axis to define a plurality of turns so that an end turn is disposed at an angle relative to the longitudinal axis, a second turn is at a first pitch angle that is less than the angle that the end turn is disposed relative to the longitudinal axis, a third turn is at a second pitch angle that is less than the first pitch angle, and a fourth turn is at a third pitch angle that is less than the second pitch angle.

2. The method of claim 1, wherein the angle that the end turn is disposed relative to the longitudinal axis is about 90°.

3. The method of claim 1, wherein the angle that the end turn is disposed relative to the longitudinal axis is greater than 90°.

4. The method of claim 1, further comprising wrapping the wave form about the longitudinal axis so that a plurality of turns are at the third pitch angle and form a central portion of the stent, the central portion of the wave form corresponding to the central portion of the stent.

5. The method of claim 1, wherein the difference between the first pitch angle and the second pitch angle is substantially the same as the difference between the second pitch angle and the third pitch angle.

6. The method of claim 1, further comprising connecting selected crowns of adjacent turns with connections.

7. The method of claim 6, wherein the connecting comprises fusing the selected crowns of adjacent turns to each other.

8. The method of claim 6, wherein the connecting comprises welding the selected crowns of adjacent turns to each other.

9. The method of claim 6, wherein the connecting comprises aligning at least some of the connections along a connection axis that defines a helix oriented in an opposite direction as the third pitch angle.

10. The method of claim 1, wherein the end portions comprise struts having different lengths to accommodate for the different pitch angles.

11. The method of claim 10, further comprising connecting an end segment to selected crowns of the first turn of the wave form.

12. The method of claim 1, wherein the wave form is formed from a wire.

13. The method of claim 1, wherein the wave form is formed from a strip of material.

\* \* \* \* \*